US00PP21885P3

(12) United States Plant Patent
Pavlich

(10) Patent No.: US PP21,885 P3
(45) Date of Patent: Apr. 26, 2011

(54) *ENSETE* PLANT NAMED 'TANDARRA RAINBOW'

(50) Latin Name: *Ensete ventricosum*
Varietal Denomination: Tandarra Rainbow

(75) Inventor: John C. Pavlich, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 92 days.

(21) Appl. No.: 12/460,983

(22) Filed: Jul. 27, 2009

(65) Prior Publication Data

US 2011/0023198 P1 Jan. 27, 2011

(51) Int. Cl.
*A01H 5/00* (2006.01)

(52) U.S. Cl. ..... Plt./373

(58) Field of Classification Search ..... Plt./373
See application file for complete search history.

*Primary Examiner* — Kent L Bell
(74) *Attorney, Agent, or Firm* — Klarquist Sparkman, LLP

(57) ABSTRACT

A new and distinct cultivar of *Ensete* plant characterized by striking strongly variegated red leaves and excellent vigor.

1 Drawing Sheet

Botanical denomination: *Ensete ventricosum.*
Variety designation: 'Tandarra Rainbow'.
Parentage: *Ensete ventricosum* 'Tandarra Red'.

BACKGROUND OF THE INVENTION

The present invention relates to a new and distinct cultivar of, *Ensete ventricosum,* and known by the cultivar name of 'Tandarra Rainbow'. The genus *Ensete* is a member of the family Musaceae. This cultivar occurred as a naturally occurring mutation in tissue culture of *Ensete ventricosum* 'Tandarra Red' (an unpatented plant) in a laboratory and was found planted out in the greenhouse in Canby, Oreg.

SUMMARY OF THE INVENTION

This new cultivar is unique and differs from its parent, *Ensete ventricosum* 'Tandarra Red', in having streaked sectorial variegation rather than no variegation. This variegation is very striking with its yellow and green shades combined with the dark red leaf edges, backs and main veins. The best comparison for variegation would be *Musa×paradisiaca* 'Ae-Ae' (an unpatented plant). The new cultivar has a similar variegation on a red rather than an all green background color.

This new cultivar has been reproduced only by asexual propagation (tissue culture). Each of the progeny exhibits identical characteristics to the parent plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photo shows a one-year-old *Ensete* 'Tandarra Rainbow' growing in a two gallon container in the warm greenhouse in June in Canby, Oreg.

DETAILED PLANT DESCRIPTION

The following is a detailed description of the new cultivar based on observations of fifteen-month-old specimen in April 2009 growing in two gallon containers in a warm greenhouse in Canby, Oreg. This greenhouse is kept at 62 to 65 degrees F. minimum and 95 degrees F. highs. The color descriptions are all based on The Royal Horticultural Society Colour Chart, 5$^{th}$ edition.

Plant:

*Type.*—Evergreen perennial.
*Form.*—Upright.
*Hardiness.*—USDA Zones 10 to 11.
*Size.*—89 cm tall and 109 cm wide.
*Habit.*—Palm-like.
*Pseudostem.*—Trunk-like, 7 cm wide and about 14 cm long, glabrous, Yellow Green 146C flushed Greyed Red 183A.

Leaf:

*Type.*—Simple.
*Number.*—5.
*Arrangement.*—Clustered on top of the pseudostem in compact rosette.
*Shape.*—Oblong.
*Venation.*—Penni-parallel.
*Margins.*—Entire.
*Apex.*—Cuspidate.
*Base.*—Attenuate and clasping.
*Size.*—63 cm long and 31 cm wide.
*Surface.*—Glabrous on both sides, leathery.
*Petiole.*—Greyed Red 185A lightening to Yellow Green 146A, grows to 28 cm long with the top 3 cm wide and the sheathing base 14 cm wide.
*Leaf color.*—Leaves top side Green N137A as the base color, with the leaf edges (from about 8 cm from margin) Greyed Purple 187A to Brown 200A and lightening with age to Greyed Purple 183A, variegated streaks are between Yellow Green 144A to N144A and lightening with age to Yellow Green 152A; bottom side is Greyed Purple 187A to Brown 200A lightening with age so the top colors show through somewhat.

Flower: Never seen.

Pests and diseases: Spider mites and aphids may be a problem. This plant has no known resistances to any pests or diseases.

I claim:

1. A new and distinct cultivar of *Ensete* plant as herein illustrated and described.

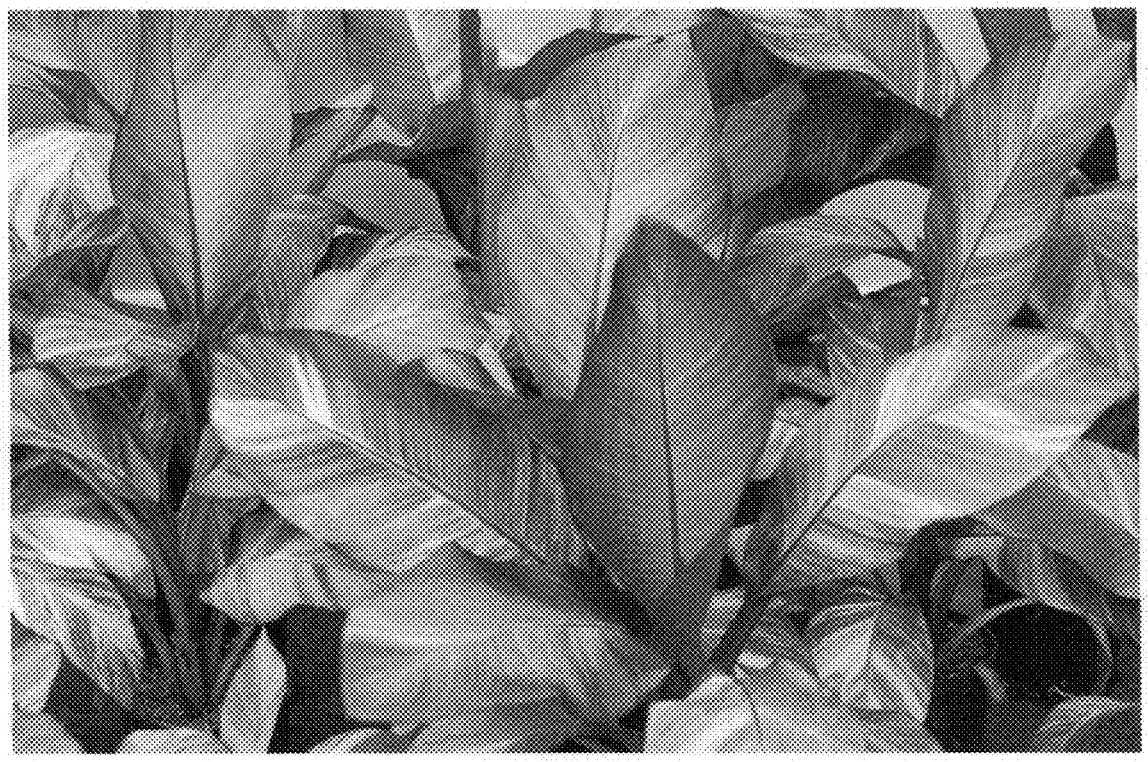

* * * * *